United States Patent [19]

Robins et al.

[11] 3,968,103

[45] July 6, 1976

[54] 1,2,3-TRIAZOLE NUCLEOSIDES

[75] Inventors: Roland K. Robins, Santa Ana; Joseph T. Witkowski, Laguna Niguel, both of Calif.

[73] Assignee: ICN Pharmaceuticals, Inc., Irvine, Calif.

[22] Filed: Sept. 28, 1972

[21] Appl. No.: 292,930

[52] U.S. Cl. .......................... 260/211.5 R; 424/180
[51] Int. Cl.² ........................................ C07H 19/04
[58] Field of Search ............................. 260/211.5 R

[56] References Cited
OTHER PUBLICATIONS

Tipson, Advances In Carbohydrate Chemistry and Biochemistry vol. 25, Academic Press, New York, N.Y., 1970 pp. 387 & 388.

Alonso et al., "Jour. Hetero. Chem." vol. 7, 1970, pp. 1269–1272.

*Primary Examiner*—Johnnie R. Brown
*Attorney, Agent, or Firm*—Lyon and Lyon

[57] ABSTRACT

Novel substituted 1,2,3-triazole nucleosides such as 4-R'-2-β-D-ribofuranosyl-1,2,3-triazole wherein R' is a nitro, carboxylic acid ester, cyano, carboxamide or thiocarboxamide group are prepared by a procedure entailing fusion of an appropriately substituted 1,2,3-triazole with a tetra-0-acyl blocked ribofuranose. The resulting compounds exhibit significant antimicrobial activity in in vitro testing or are useful in preparing compounds which exhibit such activity.

13 Claims, No Drawings

1,2,3-TRIAZOLE NUCLEOSIDES

BACKGROUND AND SUMMARY OF THE INVENTION

Nucleosides of 1,2,3-triazole substituted at position 4 of the aglycon are of interest as structural isomers of the broad spectrum antiviral nucleoside 1-β-D-ribofuranosyl-1,2,4-triazole-3-carboxamide and the analogs thereof described in our copending U.S. application Ser. No. 240,252 filed Mar. 31, 1972, now U.S. Pat. No. 3,798,209. The disclosure of that application is incorporated herein to illuminate the background of this invention. The cycloaddition of various glycosyl azides with substituted acetylenes has provided numerous examples of 1 (3)-glycosyl-1,2,3-triazoles, eg:

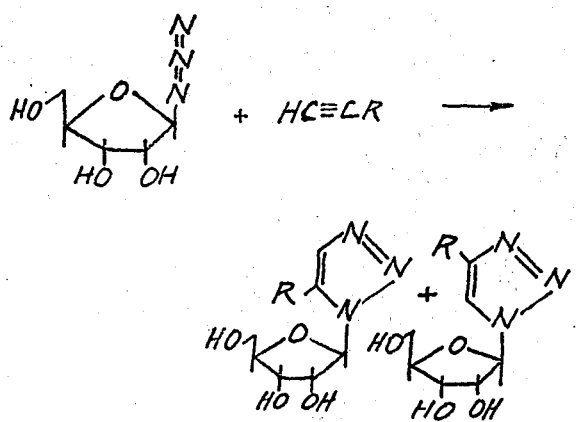

Such reactions are described, eg., in F. Michael et al. Chem. Ber. 90, 1595 (1957); J. Baddiley et al. J. Chem. Soc., 1951 (1958); Ibid. 3606; G. Garcia-Munoz et al., J. Heterocyclic Chem. 5, 699 (1968); Ibid. 6, 639 (1969); G. Alonso et al., ibid., 7, 1269 (1970); H. El Khadem et al. Cabohyd. Res., 16, 409 (1971); R. E. Harmon et al. J. Org. Chem. 36, 2553 (1971) and R. E. Harmon et al., J. Chem. Soc., Chem. Commun., 296 (1971), although in none of the foregoing publications is biological activity reported for the compounds dealt with. However, isomeric 2-glycosyl-1,2,3-triazoles (ie, compounds of structure are not accessible from azido sugars. We have now prepared a number of novel 1(2)-ribofuranosyl-1,2,3-triazoles by fusion of 1,2,3-triazole or 4-substituted 1,2,3-triazole with tetra-O-acyl blocked β-D-ribofuranose. Compounds prepared according to this invention have exhibited significant antimicrobial activity, variously against *Pseudomonas aeroginosa, Staphylococcus aureas, Escherichia coli, Streptococcus faecalis, Bacillus subtilis, Aspergillus niger* and *Candida albicans*. Preferred compounds are those of structure wherein R' is as defined above and wherein R is hydrogen or $C_1 - C_{18}$, preferably $C_1 - C_4$, acyl.

DETAILED DESCRIPTION OF THE INVENTION

The compounds of the invention are obtained by first fusing tetra-O-acyl blocked ribofuranose and appropriately substituted 1,2,3-triazoles. While essentially any acyl moiety may be employed for glycosyl blocking, workup is facilitated where the 1-O-leaving group forms a relatively volatile acid, eg, where the 1-O position of ribofuranose is blocked with a $C_1$–$C_4$ acyl group such as acetyl, propionyl or butyryl. Preferred compounds are formed according to the following schema, wherein "Ac" is acetyl and "Bz" benzoyl.

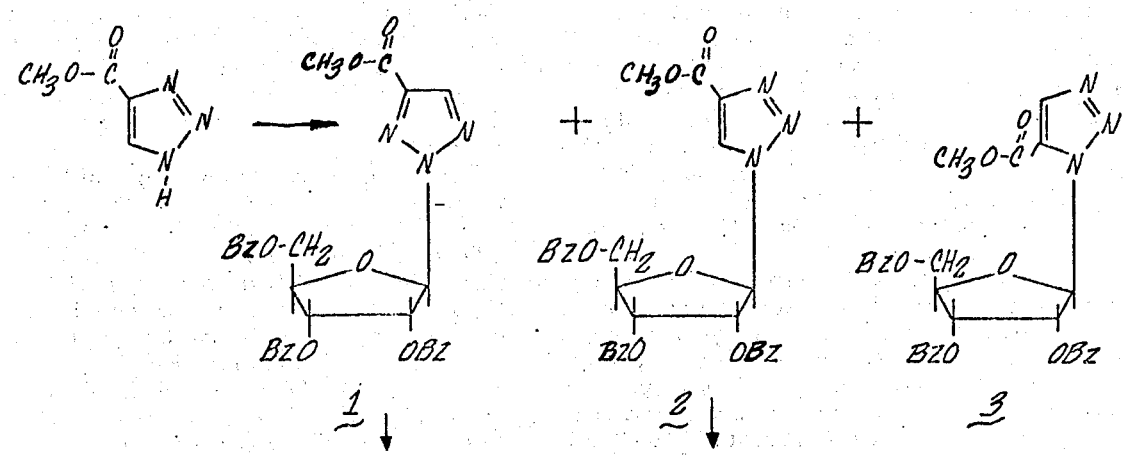

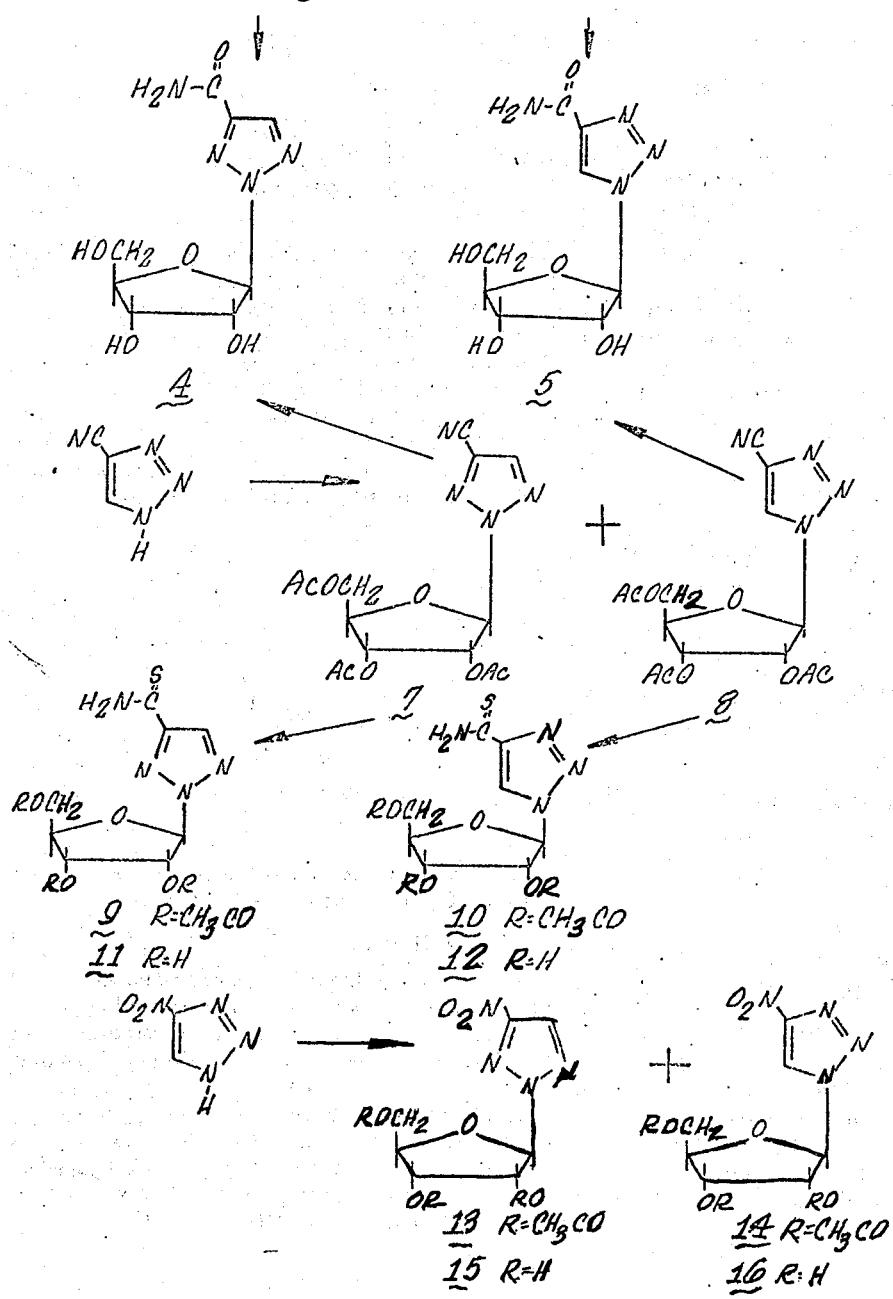

Fusion of methyl 1,2,3-triazole-4-carboxylate prepared as in F. P. Woerner et al., Chem. Ber., 103, 1908 (1970) with 1-O-acetyl-2,3,5-tri-O-benzoyl-β-D-ribofuranose in the presence of an acidic catalyst provides a mixture of 2-(2,3,5-tri-O-benzoyl-β-D-ribofuranosyl)-1,2,3-triazole-5-carboxylic acid methyl ester (1) and 1-(2,3,5-tri-O-benzoyl-β-D-ribofuranosyl)-1,2,3-triazole-4caboxylic acid methyl ester (2) in respective ratio of about 2:1, together with a small fraction of 1-(2,3,5-tri-O-benzoyl-β-D-ribofuranosyl)-1,2,3-triazole-5-carboxylic acid methyl ester. The particular carboxylic acid ester group of the starting base is not critical, as its alkoxy component is split off in the following step of conversion to the bioactive carboxamide. Again, for ease of workup, lower carboxylic acid esters such as carbomethoxy or carboethoxy groups are preferred. Treatment of 1 and 2 with methanolic ammonia provides 2-β-ribofuranosyl-1,2,3-triazole-4-carboxamide (4) and 1-β-D-ribofuranosyl-1,2,3-triazole-4-carboxamide (5). The isomeric 1-β-O-ribofuranosyl-1,2,3 -triazole-5-carboxamide may be similarly obtained from 3. If desired, glycosyl hydroxyl blocking groups may be removed before conversion to the carboxamide. For example, compound 1 may be debenzoylated by reaction with sodium methoxide is methanol.

The fusion procedure with 4-cyano-1,2,3-triazole prepared as in N. S. Zefirov et al., J. Org. Chem. (U.S.S.R.) 4, 1252 (1968) and 1,2,3,5-tetra-O-acetyl-β-D-ribofuranose affords in a 1:1 ratio 4-cyano-2-(2,3,5-tri-O-acetyl-β-D-ribofuranosyl)-1,2,3-triazole (7) and 4-cyano-1-(2,3,5-tri-O-acetyl-β-D-ribofuranosyl-)-1,2,3-triazole (8) which, through reaction with ammonia and hydrogen peroxide afford an alternate route to the nucleoside carboxamides 4 and 5 respectively. If desired, 7 and 8 may be deblocked before conversion to the corresponding carboxamides, as by treatment with alkaline reagent at low temperatures, eg, 0°C, affording the free cyano-substituted nucleoside after workup. The corresponding thiocarboxamide nucleosides are prepared by treatment of each cyano nucleoside (7 and 8) with hydrogen sulfide and triethylamine to provide, after deacylation, 2-β-D-ribofuranosyl-1,2,3-triazole-4-thiocarboxamide (11) and 1-β-D-ribofuranosyl-1,2,3-triazole-4-thiocarboxamide (12), respectively.

Fusion of 4-nitro-1,2,3-triazole prepared as in D. Pocar et al., *Gazz. Chim. Ital.*, ) 98, 949 (1968-D-ribofuranosyl-with 1,2,3,5-tetra-O-acetyl-β-D-ribofuranose in the absence of acidic catalyst provided two nucleosides 13 and 14 in a 2.4:1 ratio. The structures of these products are assigned on the basis of their nmr spectra as 4-nitro-2-(2,3,5-tri:O-acetyl-β-D-ribofuranosyl)-1,2,3-triazole (13) and 4-nitro-(2,3,5-tri-O-acetyl-β-D-ribofuranosyl)-1,2,3-triazole (14).

Treatment of 13 and 14 with sodium methoxide in methanol provides the corresponding deacylated nucleosides, 4-nitro-2-β-D-ribofuranosyl-1,2,3-triazole (15) and 4-nitro-1-β-D-ribofuranosyl-1,2,3-trizole (16).

Free nucleosides prepared according to the invention may be acylated for enhanced lipid solubility and cellular transport. In that event $C_1$-$C_{18}$, preferably $C_1$-$C_4$ acyl groups are added by reaction of glycosyl hydroxyls with the appropriate acyl halide or acid anhydride in conventional fashion.

In the examples which follow, melting points were determined on a Thomas-Hoover apparatus and are uncorrected. Evaporations were accomplished with a Buchler rotating evaporator under reduced pressure with a bath temp of 35°C. The nmr spectra were recorded at 60 MHz on a Perkin-Elmer Hitachi R20A spectrometer and chemical shifts are reported in parts per million (δ) with DDS or TMS as an internal reference. Specific rotations were determined with a Perkin-Elmer Model 141 Polarimeter. Ultraviolet spectra were determined with a Cary 15 spectrophotometer. Merck silica gel (0.05–0.2 mm) was used for chromatographic separations. All temperatures are in Centigrade degrees and, unless otherwise indicated, all parts and percentages by weight.

EXAMPLE 1

2-(2,3,5-Tri-O-benzoyl-β-D-ribofuranosyl)-1,2,3-triazole-4-carboxylic acid methyl ester (1),
1-(2,3,5-tri-O-benzoyl-β-D-ribofuranosyl)-1,2,3-triazole-4-carboxylic acid methyl ester (2) and
1-(2,3,5-tri-O-benzoyl-β-D-ribofuranosyl-1,2,3-triazole-5-carboxylic acid methyl ester (3).

Methyl 1,2,3-triazole-4-carboxylate (2.54 g, 0.020 mol) and 1-O-acetyl-2,3,5-tri-O-benzoyl-β-D-ribofuranosyl (10.1 g, 0.020 mol) and 1-0-acetyl-2,3,5-tri-0-benzoyl-β-D-ribofuranose (10.1 g, 0.020 mol) were thoroughly mixed in a mortar, then heated in an oil bath at 160° until a melt was achieved. Bis-(p-nitrophenyl)phosphate (5 mg) was added and heating in vacuo at 160°–165° was continued for 10 minutes. The residue was triturated with benzene and the insoluble product was collected and recrystallized from benzene to yield 3.00 g of 2, m.p. 189°–190°, which was identical with an authentic sample prepared by cycloaddition of the azido sugar with methyl propiolate as reported by Alonso, et al. *J Heterocyclic Chem.*, 7, 1269 (1970). The filtrate was evaporated to a syrup and the residue was crystallized from methanol to provide 3.83 g of 1: m.p. 112°–113°; $[\alpha]_D^{25}$ −57.6° (c 1.00, chloroform); nmr (DMSO-$d_6$) δ 6.87 (d, 1, $J_{1',2'}$ 2.2 Hz, 1'—H), 8.50 (s, 1, 5—H); (CDCl$_3$) δ 6.59 (d, 1, $J_{1',2'}$ 1.3 Hz, 1'—H), 8.12 (s, 1, 5—H).

Anal. Calcd for $C_{30}H_{25}N_3O_9$: C, 63.04; H, 4.41; N, 7.35. Found: C, 63.00; H, 4.46; N, 7.12.

The filtrates were combined and the solvent was removed by evaporation to leave a syrup. The syrup was dissolved in a minimum of benzene and applied to a silica gel column (5 × 70 cm) packed in benzene. The column was eluted with benzene-ether (9:1,6 liters) and fractions of 20 ml were collected. Fractions 80–120 provided an additional 2.62 g of 1, fractions 150–180 provided 200 mg of 3 which was identified by comparison with an authentic sample thereof, and fractions 213–250 provided 0.40 g of 2. Total yields of 1 and 2 were 57% and 30% respectively.

EXAMPLE 2

[A]
2-β-D-Ribofuranosyl-1,2,3-triazole-4-carboxamide (4).

Method 1. Methanol saturated with ammonia at 0° (ca 150 ml) was added to 5.71 g (0.010 mol) of 1 in a pressure bottle and kept at room temperature for 4 days. After removal of the solvent, water (30 ml) was added and the mixture was extracted with ether (six 20 ml portions). The solvent was removed and the compound crystallized from ethanol to give 2.25 g (92%) of 4: m.p. 150°–151°; $[\alpha]_D^{25}$ −59.4° (c 1.00, water); nmr (DMSO-$d_6$) δ 5.97 (d, 1, $J_{1',2'}$ 4.0 Hz, 1'—H).

Anal. Calcd for $C_8H_{12}N_4O_5$: C, 39.34; H, 4.95; N, 22.94. Found: C, 39.14; H, 4.90; N, 22.99.

Method 2. 4-Cyano-2-(2,3,5-tri-O-acetyl-β-D-ribofuranosyl)-1,2,3-triazole (7) (0.35 g, 0.001 mol) was added to 15% aqueous ammonia (30 ml) and 30% hydrogen peroxide (3 ml). After stirring at room temperature for 6 hr an additional 3 ml of 30% hydrogen peroxide was added and stirring was continued for 20 hr. Platinum black was added to destroy the excess peroxide, the solution was filtered, and the filtrate was evaporated to dryness. The residue was dissolved in a minimum of methanol and applied to a 20 × 20 cm silica gel preparative plate which was developed in ethyl acetate-methanol (9:1). The band containing 4 was removed and the compound was extracted with ethyl acetate-methanol (1:1). The solvent, along with acetamide, was removed in vacuo. The compound was dissolved in hot 2-propanol; cooling of the solution and filtering provided 14 mg of 4.

[B] 1-β-D-Ribofuranosyl-1,2,3-triazole-4-carboxamide (5).

4-Cyano-1-(2,3,5-tri-O-acetyl-β-D-ribofuranosyl-1,2,3-triazole (8). (0.35 g, 0.001 mol) was added to 15% aqueous ammonia (30 ml) and 30% hydrogen peroxide (3 ml). The solution was stirred 4 hr before additional hydrogen peroxide was added. The procedure and product isolation was identical to that used in method 2 for compound 4. The compound was dissolved in hot 2-propanol; cooling of the solution and filtering provided 30 mg of crystalline 5 which was identical to an authentic sample prepared by the procedure of Alonso, et al. *J. Heterocyclic Chem.* 7, 1269 (1970).

1-β-D-Ribofuranosyl-1,2,3-triazole-5-carboxamide (6).

Methanol (100 ml) saturated with ammonia at 0° was added to 2.05 g of 1-(2,3,5-tri-O-benzoyl-β-D-ribofuranosyl)-1,2,3-triazole-5-carboxylic acid methyl ester (6) in a glass pressure bottle. After 4 days at room temperature the solvent was removed and the residue dissolved in water (50 ml). The solution was extracted with ethyl acetate (4 × 50 ml). The water was removed in vacuo to leave a syrup which was dissolved in ethanol. After standing for several days the compound crystallized to provide 680 mg (75%) of 6: m.p. 86°–88°; $[\alpha]_D^{25}$ −59.4° (c 1.00, water); nmr (DMSO-$d_6$) δ 6.76 (d, 1, $J_{1',2'}$ 3.0 Hz, 1'—H), 8.30 (s, 1, 4—H).

Anal. Calcd for: $C_8H_{12}N_4O_5 \cdot 0.5H_2O$: C, 37.94; H, 5.17; N, 22.12. Found: C, 37.88; H, 5.09; N, 22.33.

EXAMPLE 3

4-Cyano-2-(2,3,5-tri-O-acetyl-β-D-ribofuranosyl)-1,2,3-triazole (7) and
4-Cyano-1-(2,3,5-tri-O-acetyl-β-D-ribofuranosyl)-1,2,3-triazole (8).

4-Cyano-1,2,3-triazole (0.95 g, 0.010 mol) and 1,2,3,5-tetra-O-acetyl-β-D-ribofuranose (3.18 g, 0.010 mol) were thoroughly mixed in a mortar, then heated in an oil bath at 155° until a melt was achieved. Bis-(p-nitrophenyl)phosphate (15 mg) was added and heating in vacuo at 155° was continued for 10 min. Separation of the isomers was accomplished by chromatography of the resultant syrup on a silica gel column (4.5 × 53 cm) packed in chloroform. The column was eluted with chloroform-ether (1:1, 2 liters) and fractions of 20 ml were collected. Fractions 39–52 provided 1.39 g (39%) of 7, crystallized from ethanol: m.p. 77°–79°; $[\alpha]_D^{25}$ −44.5° (c 1.00, chloroform); nmr (DMSO-$d_6$) δ 6.53 (d, 1, $J_{1',2'}$ 2.5 Hz, 1'—H), 8.81 (s, 1, 5— H); (CDCl$_3$) δ 6.32 (d, 1, $J_{1',2'}$ 3.0 Hz, 1'—H) 8.10 (s, 1, 5—H).

Anal. Calcd for $C_{14}H_{16}N_4O_7$: C, 47.73; H, 4.58; N, 15.90. Found: C, 47.78; H, 4.51; N, 15.98.

Fractions 65–95 provided 1.36 g (39%) of 8, crystallized from ethanol: m.p. 90.5°–92°; $[\alpha]_D^{25}$ −57.2° (c 1.00, chloroform); nmr (DMSO-$d_6$) δ 6.55 (d, 1, $J_{1',2'}$ 3.5 Hz, 1'—H), 9.33 (s, 1, 5—H); (CDCl$_3$) δ 6.23 (d, 1, $J_{1',2'}$ 4.0 Hz, 1'—H), 8.46 (s, 1, 5—H).

Anal. Calcd for $C_{14}H_{16}N_4O_7$: C, 47.73; H, 4.58; N, 15.90. Found: C, 47.73; H, 4.55; N, 16.04.

EXAMPLE 4

[A]
2-(2,3,5-Tri-O-acetyl-β-D-ribofuranosyl)-1,2,3-triazole-4-thiocarboxamide (9).

Hydrogen sulfide was passed through a suspension of 2.0 g of 7 in ethanol (60 ml) to which 3.5 ml of triethylamine had been added. After 2 ½ hr passage of hydrogen sulfide was ceased and the solvent was removed. The resultant syrup was dissolved in a minimum of chloroform and added to a silica gel column (2 × 38 cm) packed in chloroform. The column was eluted with chloroform (0.25 liter) and chloroform-ethyl acetate (9:1, 0.5 liter); 20 ml fractions were collected. Fractions 19–34 provided 2.6 g (98%) of 9 as a syrup; nmr (DMSO-$d_6$) δ 6.36 (d, 1, $J_{1',2'}$ 2.0 Hz, 1'—H), 8.39 (s, 1,5—H); (CDCl$_3$) δ 6.24 (d, 1, $J_{1',2'}$ 3.0 Hz, 1'—H), 8.32 (s, 1, 5—H).

[B]
1-(2,3,5-Tri-O-acetyl-β-D-ribofuranosyl)-1,2,3-triazole-4-thiocarboxamide (10).

Hydrogen sulfide was passed through a suspension of 2.0 g of 8 in ethanol (60 ml) to which 3.5 ml of triethylamine had been added. After 3 hr the passage of hydrogen sulfide gas was ceased and the solvent was removed. The product was crystallized from ethanol to give 1.90 g (86%) of 10: m.p. 110°–112°; $[\alpha]_D^{25}$ −120.6° (c 1.00, chloroform); nmr (DMSO-$d_6$) δ 6.48 (d, 1, $J_{1',2'}$ 3.5 Hz, 1'—H), 8.92 (s, 1, 5—H); (CDCl$_3$) δ 6.23 (d, 1, $J_{1',2'}$ 4.0 Hz, 1'—H), 8.58 (s, 1, 5—H).

Anal. Calcd for $C_{14}H_{18}N_4O_7S$: C, 43.52; H, 4.69; N, 14.50; S, 8.29. Found: C, 43.66; H, 4.92; H, 14.42; S, 8.35.

[C]
2-β-D-Ribofuranosyl-1,2,3-triazole-4-thiocarboxamide (11).

Sodium methoxide in methanol (60 mg of sodium in 30 ml of methanol) was added to 1.0 g of 9 and the resulting solution was stirred at room temperature for 4 hr. After neutralization with Amberlite IRC 50, the solution was filtered, and the filtrate was evaporated to dryness. Methanol and silica gel (2.5 g) were added to the syrup, and the mixture was evaporated to dryness. The silica gel mixture was added to a dry-packed silica gel column (1 × 18 cm) and the column was eluted with chloroform (0.1 liter), ethylacetate-chloroform (1:1, 0.1 liter) and ethyl acetate (0.4 liter); 20 ml fractions were collected. Fractions 14–28 provided 0.61 g (91%) of 11 as a syrup: nmr (DMSO-$d_6$) δ 5.95 (d, 1, $J_{1',2'}$ 4.0 Hz, 1'—H), 8.32 (s, 1, 5—H).

Anal. Calcd for $C_8H_{12}N_4O_4S$: C, 36.93; H, 4.65; N, 21.53; S, 12.30. Found: C, 37.04; H, 4.48; N, 21.24; S, 12.00.

[D]
1-β-D-Ribofuranosyl-1,2,3-triazole-4-thiocarboxamide (12).

1-(2,3,5-Tri-O-acetyl-β-D-ribofuranosyl)-1,2,3-triazole-4-thiocarboxamide (1.0 g) was added to sodium methoxide in methanol (60 mg of sodium in 30 ml of methanol) and the resulting solution was stirred at room temperature for 4 hr. After neutralization of the solution with Amberlite IRC 50, the solution was filtered, and the filtrate was evaporated to dryness. The product was crystallized from ethanol to give 0.55 g (82%) of 12: m.p. 152°–154°; $[\alpha]_D^{25}$ −85.2° (c 1.00, water); nmr (DMSO-$d_6$) δ 6.04 (d, 1, $J_{1',2'}$ 4.8 Hz, 1'—H), 8.90 (s, 1, 5—H).

Anal. Calcd for $C_8H_{12}N_4O_4S$: C, 36.93; H, 4.65; N, 21.53; S, 12.30. Found: C, 37.09; H, 4.69; N, 21.41; S, 12.16.

EXAMPLE 5

[A]
4-Nitro-2-(2,3,5-tri-O-acetyl-β-D-ribofuranosyl)-1,2,3-triazole (13) and
4-Nitro-1-(2,3,5-tri-O-acetyl-β-D-ribofuranosyl-1,2,3-triazole (14).

4-Nitro-1,2,3-triazole (8.55 g, 0.075 mol) and 1,2,3,5-tetra-O-acetyl-β-D-ribofuranose (23.85 g, 0.075 mol) were mixed in a mortar, then heated in vacuo (ca 20 mm) in an oil bath at 175° for 45 min. The syrup was dissolved in a minimum of chloroform and applied to a silica gel column (5.5 × 88 cm) packed in chloroform. The column was eluted with chloroform-ethyl acetate (9:1, 7 liters) and fractions of 20 ml were collected. Fractions 104–160 provided 16.15 g (58%) of 13 as a syrup: $[\alpha]_D^{25}$ −37.3° (c 1.13, chloroform); nmr (DMSO-$d_6$) δ 6.52 (d, 1, $J_{1',2'}$ 2.4 Hz, 1'—H), 8.93 (s, 1, 5—H); (CDCl$_3$) δ 6.24 ld 1, $J_{1',2'}$ 3.5 Hz, 1'—H), 8.27 (s, 1, 5—H).

Anal. Calcd for $C_{13}H_{16}N_4O_9$: C, 41.97; H, 4.34; N, 15.06. Found: C, 41.75; H, 4.51; N, 14.94.

Fractions 225–300 provided 6.81 g (24%) of 14 which was crystallized from ethanol: m.p. 100°–102°; $[\alpha]_D^{25}$ −59.1° (c 1.00, chloroform); nmr (DMSO-$d_6$) δ 6.52 (d, 1, $J_{1',2'}$ 3.0 Hz, 1'—H), 9.57 (s, 1, 5—H); (CDCl$_3$) δ 6.27 (d, 1, $J_{1',2'}$ 4.0 Hz, 1'—H), 8.68 (s, 1, 5—H).

Anal. Calcd for $C_{13}H_{16}N_4O_9$: C, 41.97; H, 4.34; N, 15.06. Found: C, 42.02; H, 4.38; N, 15.29.

[B] 4-Nitro-2-β-D-ribofuranosyl-1,2,3-triazole (15).

A solution of sodium methoxide (from 200 mg of sodium) in methanol (150 ml) was added to 13 (11.16 g, 0.03 mol). The solution was stirred at room temperature for 15 hrs and then was neutralized with Bio-Rad AG 50W X-2 (H). The resin was removed by filtration and the solvent was removed by evaporation in vacuo. Crystallization of the product from 2-propanol-ethanol (4:1) provided 6.2 g (84%) of 15: m.p. 147–148° $[\alpha]_D^{25}$ −59.8° (c 1.00, water); nmr (DMSO-$d_6$) δ 5.96 (d, 1, $J_{1',2'}$ 3.5 Hz, 1'—H), 8.75 (s, 1,5—H).

Anal. Calcd for $C_7H_{10}N_4O_6$: C, 34.15; H, 4.09; N, 22.76. Found: C, 34.18; H, 4.08; N, 22.78.

[C] 4-Nitro-1-β-D-ribofuranosyl-1,2,3-triazole (16).

A solution of 14 (3.72 g, 0.01 mol) and sodium methoxide (from 150 mg of sodium) in methanol (50 ml) was stirred at room temperature for 4 hrs. The solution was neutralized with Bio-Rad Ag X-2 (H) and the resin removed by filtration. The solvent was removed and the compound was crystallized from ethanol-ethyl acetate (1:4) to give 2.1 g (85%) of 16: m.p. 172°–174°; $[\alpha]_D^{25}$ −66.3° (c 1.00, water); nmr (DMSO-$d_6$) δ 6.03 (d, 1, $J_{1',2'}$ 3.5 Hz, 1'—H), 9.44 (s, 1, 5—H).

Anal. Calcd for $C_7H_{10}N_4O_6$: C, 34.15; H, 4.09; N, 22.76. Found: C, 33.95; H, 4.35; N, 22.78.

[D] 4-Amino-2-β-D-ribofuranosyl-1,2,3-triazole (17).

A solution of 15 (2.46 g, 0.01 mol) in methanol (50 ml) and 5% palladium-on-carbon catalyst (500 mg) was stirred at room temperature while a solution of 99% hydrazine hydrate in methanol (1:3, v/v) was added dropwise until evolution of nitrogen ceased. The catalyst was removed by filtration through Celite and the solvent was removed by evaporation in vacuo to give 2.30 g of syrup. The syrup was dissolved in methanol and absorbed on 5 g of silica gel. The methanol was removed and the mixture was added to a dry packed silica gel column (2.5 × 28 cm). The column was eluted with chloroform (0.2 liter), chloroform-ethyl acetate (1:1, 0.2 liter), ethyl acetate (0.2 liter), and ethyl acetate-methanol (9:1, 0.5 liter); 20 ml fractions were collected. Fractions 30–35 provided 2.0 g (93%) of 17 as a syrup: nmr (DMSO-$d_6$) δ 5.62 (d, 1, $J_{1',2'}$ 4.0 Hz, 1'—H), 7.03 (s, 1, 5—H).

Anal. Calcd for $C_7H_{12}N_4O_4$: C, 38.89; H, 5.59; N, 25.92. Found: C, 38.64; H, 5.81; N, 25.71.

[E] 4-Amino-1-β-D-ribofuranosyl-1,2,3-triazole (18).

A solution of 16 (1.23 g, 0.005 mol) in methanol (25 ml) and 5% palladium-on-carbon catalyst (250 mg) was stirred at room temperature while a solution of 99% hydrazine hydrate in methanol (1:3, v/v) was added dropwise until evolution of nitrogen ceased. The catalyst was removed by filtration through Celite and the solvent was removed. The product was crystallized from ethyl acetate-methanol (3:1) to give 1.0 g (92%) of 18, m.p. 102°–104°. The nmr spectrum indicated the presence of ethyl acetate. After heating at 100° in vacuo overnight 18 had a melting point of 141°–143°: $[\alpha]_D^{25}$ −65.8° (c 1.00, water); nmr (DMSO-$d_6$) δ 5.77 (d, 1, $J_{1',2'}$ 4.0 Hz, 1'—H), 7.34 (s, 1, 5—H).

Anal. Calcd for $C_7H_{12}N_4O_4$: C, 38.89; H, 5.59; N, 25.92. Found: C, 38.67; H, 5.51; N, 26.04.

[F] 2-(2,3,5-Tri-O-acetyl-β-D-ribofuranosyl)-1,2,3-triazole (19) and 1-(2,3,5-tri-O-acetyl-β-D-ribofuranosyl)-1,2,3-triazole (20).

A mixture of 1,2,3-triazole (166 g, 0.024 mol) and 1,2,3,5-tetra-O-acetyl-β-D-ribofuranose (6.36 g, 0.020 mol) was heated in an oil bath at 145° until a melt was achieved. Bis-(p-nitrophenyl)phosphate (20 mg) was added and heating was continued for 2 hrs. The syrup was cooled, dissolved in chloroform (75 ml) and washed with aqueous 5% sodium bicarbonate (25 ml). The chloroform layer was separated and dried over anhydrous magnesium sulfate. The drying agent was removed by filtration and the solvent was removed. The syrup was applied to a silica gel column (2.5 × 80 cm) packed in methylene chloride. Elution was with methylene chloride-ethyl acetate (9:1, 4 liters) and fractions of 20 ml were collected.

Fractions 50–62 provided 0.68 g of syrup which was shown by nmr to be 19 with a small amount of unreacted sugar: nmr (DMSO-$d_6$) δ 6.34 (d, 1, $J_{1',2'}$ 3.0 Hz, 1'—H), 8.01 (s, 2; 4,5—H); (CDCl$_3$) δ 6.25 (d, 1, $J_{1',2'}$ 2.0 Hz, 1'—H), 7.68 (s, 2; 4,5—H).

Fractions 82–160 provided 3.5 g (53%) of 20 as a syrup; nmr (DMSO-$d_6$) δ 6.42 (d, 1, $J_{1',2'}$ 3.3 Hz, 1'—H), 7.86 (d, 1, $J_{4,5}$ ca. 1, 4—H), 8.37 (d, 1, $J_{4,5}$ ca. 1, 5—H); (CDCl$_3$) δ 6.20 (d, 1, $J_{1',2'}$ 3.0 Hz, 1'—H), 7.75 (d, 1, $J_{4,5}$ ca. 1, 4—H), 7.77 (d, 1, $J_{4,5}$ ca. 1, 5—H).

Anal. Calcd for $C_{13}H_{17}N_3O_7$: C, 47.71; H, 5.23; N, 12.84. Found: C, 47.53; H, 5.21; N, 12.63.

[G] 2-β-D-Ribofuranosyl-1,2,3-triazole (21).

Method 1. A solution of 17 (0.43 g, 0.002 mol) and 50% hypophosphorous acid (1.31 g, 0.01 mol) in water (5 ml) was kept at 35°–40° while sodium nitrite (150 mg) in water (3 ml) was added dropwise. The reaction was kept at 35° for 30 min. and the solvent was removed. The syrup was dissolved in methanol and absorbed on silica gel (3 g). The methanol was removed and the mixture was applied to a silica gel column (1.5 × 32 cm) packed in chloroform. Elution was with chloroform (0.1 liter), chloroform ethyl acetate (1:1, 0.2 liter) and ethyl acetate (0.5 liter) and fractions of 20 ml were collected. Fractions 20–27 provided 200 mg (50%) of 21 as a syrup: nmr (DMSO-$d_6$) δ 5.93 (d, 1, $J_{1',2'}$ 3.8 Hz, 1'— H), 7.89 (s, 2; 4, 5—H).

Anal. Calcd for $C_7H_{11}N_3O_4$: C, 41.79; H, 5.51; N, 20.89. Found: C, 41.89; H, 5.43; N, 20.65.

Method 2. A solution of sodium methoxide (from 50 mg of sodium) in methanol (60 ml) was added to 19 (630 mg) and the solution was stirred at room temperature for 3 hr. The solution was neutralized with Amberlite IRC 50; the resin was removed by filtration. The syrup obtained upon removal of the solvent was dissolved in methanol and absorbed on silica gel (2 g). The methanol was removed and the mixture was added to a silica gel column (1 × 20 cm) packed in chloroform. Elution was with chloroform (0.1 liter), chloroform-ethyl acetate (1:1, 0.1 liter), and ethyl acetate-methanol (9:1, 0.2 liter); fractions of 20 ml were collected. Fractions 11–14 provided 330 mg (85%) of 21 which was identical to that prepared by Method 1.

[H] 1-β-D-Ribofuranosyl-1,2,3-triazole (22).

A solution of sodium methoxide (from 120 mg of sodium) in methanol (50 ml) was added to 20 (1.0 g). The solution was stirred at room temperature for 4 hours and then neutralized with Bio-Rad AG 50W X-2 (H). The solution was filtered and the solvent was removed. The syrup was dissolved in methanol and absorbed on silica gel (3 g). After removal of the methanol the mixture was added to a silica gel column (1 × 20 cm) packed in chloroform. Elution was with chloroform (20 ml), chloroform-ethyl acetate (1:1, 40 ml), ethyl acetate (40 ml), and ethyl acetate-methanol (9:1, 100 ml); fractions of 20 ml were collected. Fractions 8–12 contained the product which was crystallized from ethyl acetate-ethanol (3:1) to provide 200 mg (33%) of 22: m.p. 123°–125°; $[\alpha]_D^{25}$ −48.9° (c 1.00, water); nmr (DMSO-$d_6$) δ 6.00 (d, 1, $J_{1'\,,2'}$ 4.2 Hz, 1'—H), 7.80 (d, 1, $J_{4,5}$ ca. 1 Hz, 4-H), 8.35 (d, 1, $J_{4,5}$ ca. 1 Hz, 5—H).

Anal. Calcd for $C_7$-tri-O-acetyl-β3$O_4$: C, 41.79; H, 5.51; N, 20.89. Found: C, 41.71; H, 5.32; N, 20.98.

EXAMPLE 6

Compounds prepared according to the foregoing Examples were assayed for antimicrobial activity according to the following protocol. The microorganism is transferred from a stock culture, suspended in a nutrient broth and incubated overnight. After mixing, a small aliquot (ca. 0.02 ml) of the liquid culture is transferred to a second tube of a nutrient broth and again mixed. One such tube is prepared for each petri dish to be inoculated.

Prior to inoculation, a solid nutrient medium is prepared and poured in the petri dish, allowed to cool and harden, and then inoculated by pouring the previously prepared suspension of micro-organisms on the surface. After approximately 5 minutes, the suspension is poured off, and the petri dish is inverted and allowed to dry for 45–60 min.

The petri dishes have a grid of 1 cm squares impressed into the bottom half which contains the nutrient medium. The rows and columns of squares are identified by alphabetic characters (A–G) and numerals (1–7) respectively. Each test compound may thus be assigned a singular location (e.g., C-3, A-5, etc.).

A flame-cleaned microspatula is used to transfer enough compound to cover a small pin head to its given location after inoculation of the organism as above. Compounds are tested on three petri dishes for each organism.

The dishes are incubated at room temperature for 24–48 hours. An active compound inhibits the growth of the organism and so a circular clear area (zone of inhibition) is seen around the compound when viewed against a dark background or in an oblique light.

Zones of inhibition are measured by eye and are as follows:

| 0 | none | | 4+ | 1.5 | cm |
|---|---|---|---|---|---|
| ± | 0.25 | cm | 5+ | 2.0 | cm |
| + | 0.5 | cm | 6+ | 2.5 | cm |
| 2+ | 0.75 | cm | 7+ | 3.0 | cm |
| 3+ | 1.0 | cm | 8+ | ca. ½ | dish |

Active compounds are as reported in the Table which follows.

TABLE

ANTIMICROBIAL ACTIVITY IN VITRO

| Microorganism | Compound No. | | | |
|---|---|---|---|---|
| | 4 | 11 | 15 | 16 |
| Pseudomonas aeroginosa | +5 | — | — | — |
| Staphylococcus aureus | — | — | +4 | +3 |
| Escherichia coli | +5 | — | +4 | +3 |
| Streptococcus faecalis | — | — | +4 | +3 |
| Bacillus subtilis | — | — | +3 | +3 |
| Aspergillus niger | — | +5 | — | — |
| Candida albicans | — | +2 | — | — |

Compound 15 was also active against the insect form of the parasite Trypanosoma cruzi at 100 mg/ml in broth dilution assay and exhibited antifertility effects at 10 mg/kg × 3 when subcutaneously injected into rats.

We claim:

1. A 1,2,3-triazole nucleoside of structure

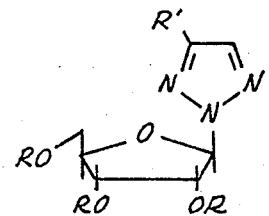

wherein R is hydrogen acetyl or benzoyl and R' is selected from the group consisting of nitro, carboxamido, thiocarboxamido, cyano and carbomethoxy groups.

2. An N-β-D-ribofuranosyl nucleoside of structure

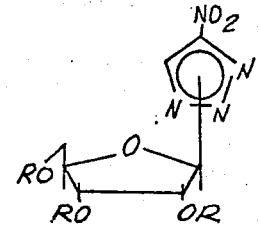

wherein R is hydrogen or acetyl.

3. 2-(2,3,5-tri-O-benzoyl-β-D-ribofuranosyl)-1,2,3-triazole-4-carboxylic acid methyl ester.

4. 2-β-D-ribofuranosyl-1,2,3-triazole-4-carboxylic acid methyl ester.

5. 2-β-D-Ribofuranosyl-1,2,3-triazole-4-carboxamide.

6. 4-Cyano-2-(2,3,5-tri-O-acetyl-β-D-ribofuranosyl)-1,2,3-triazole.

7. 4-Cyano-2-β-D-ribofuranosyl-1,2,3-triazole.

8. 2-(2,3,5-tri-0-acetyl-β-D-ribofuranosyl)-1,2,3-triazole-4-thiocarboxamide.

9. 2-β-D-Ribofuranosyl-1,2,3-triazole-4-thiocarboxamide.

10. 4-Nitro-2-(2,3,5-tri-O-acetyl-β-D-ribofuranosyl)-1,2,3-triazole.

11. 4-Nitro-1-(2,3,5-tri-O-acetyl-β-D-ribofuranosyl)-1,2,3-triazole.

12. 4-Nitro-2-β-D-ribofuranosyl-1,2,3-triazole.

13. 4-Nitro-1-β-D-ribofuranosyl-1,2,3-triazole.

* * * * *